(12) United States Patent
Yamashita

(10) Patent No.: US 8,383,863 B2
(45) Date of Patent: Feb. 26, 2013

(54) METHOD FOR PRODUCING ALDEHYDE AND KETONE

(75) Inventor: Miyoshi Yamashita, Joetsu (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 148 days.

(21) Appl. No.: 13/101,318

(22) Filed: May 5, 2011

(65) Prior Publication Data

US 2011/0282102 A1 Nov. 17, 2011

(30) Foreign Application Priority Data

May 13, 2010 (JP) ................. 2010-111041

(51) Int. Cl.
*C07C 45/29* (2006.01)

(52) U.S. Cl. ....................... 568/383; 568/449

(58) Field of Classification Search .................. 568/383, 568/489

See application file for complete search history.

(56) References Cited

FOREIGN PATENT DOCUMENTS

| JP | 5-302049 | 11/1993 |
|---|---|---|
| JP | 6-116216 | 4/1994 |
| JP | 2007-154024 | 6/2007 |

OTHER PUBLICATIONS

"1.1 Oxidation from Alcohol, a DMSO-DCC Method"; Translation of Lectures on Experimental Chemistry, 4th Edition, vol. 21; Published by Maruzen Co., Ltd.; pp. 11-13; 4 sheets.

Pfitzner, K.E., et al.; "A New and Selective Oxidation of Alcohols"; Communications to the Editor; Oct. 5, 1963; pp. 3027-3028.

Sheehan, J.C., et al.; "A Convenient Synthesis of Water-Soluble Carbodiimides"; Notes A department for short papers of immediate interest; vol. 26; Jul., 1961; pp. 2525-2528.

Weinshenker, N.M., et al.; "Polymeric Carbodiimide, Moffat Oxidation: 4-tert-Butycyclohexanone"; Organic Syntheses; Coll. vol. 6, p. 218 (1988); vol. 56; p. 99 (1977); 3 pages.

Extended European Search Report for Application No. 11165376.2, mailed Sep. 29, 2011.

Jones, J.B., et al.; "Steroids and Steroidases: III. Dicyclohexylcarbodiimide-dimethyl Sulfoxide Oxidations of Alcohols and Thios"; Canadian Journal of Chemistry; vol. 44; No. 21; Nov. 1, 1966; pp. 2517-2523; XP055007342.

*Primary Examiner* — Sikarl Witherspoon

(74) *Attorney, Agent, or Firm* — Alston & Bird LLP

(57) ABSTRACT

Provided is a highly efficient method for the production of aldehydes and ketones, which is inexpensive, exhibits high reactivity, and is capable of easy separation of byproduct after the reaction. More particularly, there is provided a method for producing an aldehyde or a ketone, comprising at least an oxidation step of oxidizing a primary alcohol or a secondary alcohol in the presence of a polymeric carbodiimide represented by the following formula (1) and having a weight-average molecular weight of 300 to 5000, and a sulfoxide compound, together with an acid and a base, or together with a salt of the acid and the base.

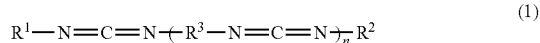

(1)

17 Claims, No Drawings

METHOD FOR PRODUCING ALDEHYDE AND KETONE

BACKGROUND OF THE INVENTION

1. Field of the Invention

The present invention relates to a method for producing an aldehyde or a ketone, which is useful in the field of organic synthetic chemistry, through an oxidation reaction of an alcohol under a mild condition, along with easy removal of a byproduct.

2. Description of the Related Art

Extensive investigations have been hitherto conducted on the reactions of oxidizing a primary alcohol into an aldehyde, and oxidizing a secondary alcohol into a ketone, in view of the usefulness of aldehydes and ketones in the field of organic synthesis. Among these oxidation reactions, Pfitzner-Moffatt oxidation by which an oxidation reaction of an alcohol is carried out using dicyclohexylcarbodiimide (hereinafter, abbreviated to "DCC"), dimethyl sulfoxide (hereinafter, abbreviated to "DMSO") and an acid, has been reported as one of effective oxidation reactions that can be carried out under mild reaction conditions of room temperature and near neutrality, without using a highly toxic heavy metal oxidizing agent or an explosive oxidizing agent (K. E. Pfitzner and J. G. Moffatt, J. Am. Chem. Soc., 85, 3027 (1963)).

However, in this reaction, since dicyclohexylurea generated from DCC after the reaction exhibits some dissolubility in those solvents generally used in oxidation reactions, such as DMSO, benzene and toluene, there is a need for a method of precipitating such a urea compound by exchanging the solvent with a solvent having low dissolvability for the urea compound after the reaction, and removing the resulting precipitate through filtration. Furthermore, this method requires complicated operations, and it is difficult to completely separate the urea compound that is produced as a byproduct (Lectures on Experimental Chemistry, 4th Edition, Vol. 21, 1.1 "Oxidation from Alcohol, a. DMSO-DCC Method", p. 11-13, published by Maruzen Co., Ltd.).

Meanwhile, there have been reports on the methods which can be used to facilitate the separation of these urea compounds that are produced as byproducts from carbodiimide compounds. One method is reported to involve the use of a water-soluble carbodiimide such as 1-ethyl-3-(3-N,N-dimethylaminopropyl)-carbodiimide (hereinafter, abbreviated to "EPCI") or hydrochloride thereof, so that the urea compound that is produced as a byproduct after the reaction can be removed by extraction with water (J. C. Sheehan, P. A. Cruickshank, and G. L. Boshart, J. Org. Chem. Soc., 26, 2525 (1961) and Japanese Patent Application Unexamined Publication No. 6-116216).

Furthermore, another method has been reported, which is a method of introducing a carbodiimide group into the aromatic ring of polystyrene that has been crosslinked with divinylbenzene, such as an N-alkylcarbodiimide polystyrene resin, to make the resin insoluble in the reaction solvent, so that the urea compound produced as a byproduct after the reaction can be removed by filtration (for example, N-cyclohexylcarbodiimide polystyrene resin, manufactured by Tokyo Chemical Industry Co., Ltd.) (Organic Synthesis, Vol. 56, 99 (1977)).

SUMMARY OF THE INVENTION

However, some problems have been recognized in the aldehyde production methods using two types of carbodiimides as described above.

First, EPCI and the like necessitate very expensive raw materials for their synthesis and have low storage stability, so that use of these carbodiimide compounds in an industrial scale is not favorable. Furthermore, EPCI and the like are less reactive compared with DCC, and have a problem in that implementation of the reaction for a long time or increase in byproducts results in decrease in the yield.

Furthermore, since a N-alkylcarbodiimide polystyrene resin needs multi-stage synthesis reactions based on polystyrene for its production. Accordingly, the product yield is low, the product is expensive, and the carbodiimide equivalent of the resulting resin is low as well. Also, since the N-alkylcarbodiimide polystyrene resin thus obtained is in the form of polymeric powder which is insoluble in the reaction solvent, the resin has low reactivity and it is not favorable to use the resin in the oxidation method that is implemented in an industrial scale.

The present invention has been made in view of such circumstances, and solves the problems of the conventional technologies by providing a highly efficient method for the production of aldehydes and ketones, which is inexpensive, exhibits high reactivity, and is capable of the separation of byproduct after the reaction.

According to the present invention, there is provided a method for producing an aldehyde or a ketone, comprising at least an oxidation step of oxidizing a primary alcohol or a secondary alcohol in the presence of a polymeric carbodiimide being represented by the following formula (1), having a weight-average molecular weight of 300 to 5000 and being soluble in an organic solvent, and a sulfoxide compound, together with an acid and a base, or together with a salt of the acid and the base.

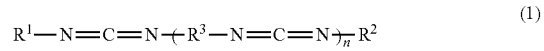

(1)

wherein $R^1$ and $R^2$, which may be identical with or different from each other, each represents a substituted or unsubstituted, linear or branched alkyl group having 1 to 12 carbon atoms, a substituted or unsubstituted cycloalkyl group having 3 to 12 carbon atoms, or a substituted or unsubstituted aryl group having 6 to 12 carbon atoms; $R^3$ represents a substituted or unsubstituted, linear or branched alkylene group having 1 to 12 carbon atoms, a substituted or unsubstituted cycloalkylene group having 3 to 12 carbon atoms, a substituted or unsubstituted arylene group having 6 to 12 carbon atoms, a substituted or unsubstituted alkylenecycloalkylene group having 4 to 18 carbon atoms, or a substituted or unsubstituted alkylenearylene group having 7 to 18 carbon atoms; and n represents a number that satisfies the molecular weight described above.

According to the production method of the present invention, an aldehyde or a ketone, which is useful in the field of organic synthetic chemistry, can be produced with high yield under a mild condition, and a urea compounds as a byproduct can be easily removed by filtration or the like.

DETAILED DESCRIPTION

Hereinafter, the present invention will be described in more detail.

The primary alcohol and the secondary alcohol are preferably alcohols represented by the following formulas (2) and (3), respectively.

(2)

(3)

wherein R⁴ represents a linear, branched or cyclic hydrocarbon group having 1 to 20 carbon atoms; and $R^5$ and $R^6$, which may be identical with or different from each other, each independently represents a linear, branched or cyclic hydrocarbon group having 1 to 20 carbon atoms, or may be joined together to form a ring.

Specific examples of the aldehyde that may be obtained from a primary alcohol include linear saturated aldehydes, linear unsaturated aldehydes, branched saturated aldehydes, branched unsaturated aldehydes and aromatic aldehydes.

Examples of the linear saturated aldehydes include 1-hexyl aldehyde derived from 1-hexyl alcohol, 1-octyl aldehyde derived from 1-octyl alcohol, 1-decyl aldehyde derived from 1-decyl alcohol, 1-dodecyl aldehyde derived from 1-dodecyl alcohol, 1-tetradecyl aldehyde derived from 1-tetradecyl alcohol, 1-hexadecyl aldehyde derived from 1-hexadecyl alcohol, and 1-octadecyl aldehyde derived from 1-octadecyl alcohol.

Examples of the linear unsaturated aldehydes include Z-5-decenyl aldehyde derived from Z-5-decenyl alcohol, Z-8-dodecenyl aldehyde derived from Z-8-dodecenyl alcohol, Z-9-dodecenyl aldehyde derived from Z-9-dodecenyl alcohol, Z-7-tetradecenyl aldehyde derived from Z-7-tetradecenyl alcohol, Z-9-tetradecenyl aldehyde derived from Z-9-tetradecenyl alcohol, Z-11-tetradecenyl aldehyde derived from Z-11-tetradecenyl alcohol, Z-7-hexadecenyl aldehyde derived from Z-7-hexadecenyl alcohol, Z-9-hexadecenyl aldehyde derived from Z-9-hexadecenyl alcohol, Z-10-hexadecenyl aldehyde derived from Z-10-hexadecenyl alcohol, E-10-hexadecenyl aldehyde derived from E-10-hexadecenyl alcohol, Z-11-hexadecenyl aldehyde derived from Z-11-hexadecenyl alcohol, E-11-hexadecenyl aldehyde derived from E-11-hexadecenyl alcohol, Z-11-octadecenyl aldehyde derived from Z-11-octadecenyl alcohol, Z-13-octadecenyl aldehyde derived from Z-13-octadecenyl alcohol, E,E-2,6-octadienal derived from E,E-2,6-octadienol, E,Z-2,4-octadienal derived from E,Z-2,4-octadienol, E,E-2,4-nonadienal derived from E,E-2,4-nonadienol, E,E,Z-2,4,6-nonatrienal derived from E,E,Z-2,4,6-nonatrienol, E,E-2,4-decadienal derived from E,E-2,4-decadienol, E,Z-8,10-dodecadienal derived from E,Z-8,10-dodecadienol, Z,E-5,7-dodecadienal derived from Z,E-5,7-dodecadienol, E,Z-4,9-tetradecadienal derived from E,Z-4,9-tetradecadienol, Z-11,13-tetradecadienal derived from Z-11,13-tetradecadienol, Z,E-9,11,13-tetradecatrienal derived from Z,E-9,11,13-tetradecatrienol, E,Z-4,6-hexadecadienal derived from E,Z-4,6-hexadecadienol, Z,Z-7,11-hexadecadienal derived from Z,Z-7,11-hexadecadienol, Z,Z-11,13-hexadecadienal derived from Z,Z-11,13-hexadecadienol, E,E,Z-4,6,11-hexadecatrienal derived from E,E,Z-4,6,11-hexadecatrienol, and Z,Z,E-7,11,13-hexadecatrienal derived from Z,Z,E-7,11,13-hexadecatrienol.

Examples of the branched saturated aldehydes include 2,7-dimethyloctyl aldehyde derived from 2,7-dimethyloctyl alcohol, 3,7-dimethyloctyl aldehyde derived from 3,7-dimethyloctyl alcohol, 4,5-dimethyldecyl aldehyde derived from 4,5-dimethyldecyl alcohol, 4,8-dimethyldecyl aldehyde derived from 4,8-dimethyldecyl alcohol, and 2-ethyldodecyl aldehyde derived from 2-ethyldodecyl alcohol.

Examples of the branched unsaturated aldehydes include 2,6-dimethyl-5-heptenal derived from 2,6-dimethyl-5-heptenol, 14-methyl-Z-8-hexadecenal derived from 14-methyl-Z-8-hexadecenol, 3,7-dimethyl-E-2,6-octadienal derived from 3,7-dimethyl-E-2,6-octadienol, 3,7,11-trimethyl-E-6,10-dodecadienal derived from 3,7,11-trimethyl-E-6,10-dodecadienol, geranial derived from geraniol, and citronellal derived from citronellol.

Examples of the aromatic aldehydes include benzaldehyde derived from benzyl alcohol, 3-methylbenzaldehyde derived from 3-methylbenzyl alcohol, 4-methylbenzaldehyde derived from 4-methylbenzyl alcohol, and 4-isopropylbenzaldehyde derived from 4-isopropylbenzyl alcohol.

Specific examples of the ketone that may be obtained from a secondary alcohol include linear saturated ketones, linear unsaturated ketones, branched saturated ketones, branched unsaturated ketones, cyclic saturated ketones, and cyclic unsaturated ketones.

Examples of the linear saturated ketones include 2-hexanone derived from 2-hexanol, 3-hexanone derived from 3-hexanol, 2-octanone derived from 2-octanol, 3-octanone derived from 3-octanol, 2-nonanone derived from 2-nonanol, 3-nonanone derived from 3-nonanol, 4-nonanone derived from 4-nonanol, 2-decanone derived from 2-decanol, 3-decanone derived from 3-decanol, 2-dodecanone derived from 2-dodecanol, and 3-dodecanone derived from 3-dodecanol.

Examples of the linear unsaturated ketones include E-3-nonen-2-one derived from E-3-nonen-2-ol, Z-6-nonen-2-one derived from Z-6-nonen-2-ol, E-7-decen-2-one derived from E-7-decen-2-ol, 1-dodecen-3-one derived from 1-dodecen-3-ol, E-7-tetradecen-2-one derived from E-7-tetradecen-2-ol, 1-hexadecen-3-one derived from 1-hexadecen-3-ol, Z-7-octadecen-11-one derived from Z-7-octadecen-11-ol, Z-12-nonadecen-11-one derived from Z-12-nonadecen-11-ol, Z-13-icosen-10-one derived from Z-13-icosen-10-ol, Z-6-heneicosen-11-one derived from Z-6-heneicosen-11-ol, and Z-14-tricosen-10-one derived from Z-14-tricosen-10-ol.

Examples of the branched saturated ketones include 2-methyl-4-heptanone derived from 2-methyl-4-heptanol, 4-methyl-3-heptanone derived from 4-methyl-3-hehptanol, 4,6-dimethyl-3-octanone derived from 4,6-dimethyl-3-octanol, 4-methyl-5-nonanone derived from 4-methyl-5-nonanol, 5-ethyl-4-nonanone derived from 5-ethyl-4-nonanol, 4,6,8-trimethyl-2-decanone derived from 4,6,8-trimethyl-2-decanol, and 3,7,11-trimethyl-5-dodecanone derived from 3,7,11-trimethyl-5-dodecanol.

Examples of the branched unsaturated ketones include 4-methyl-E-4-hexen-3-one derived from 4-methyl-E-4-hexen-3-ol, 5-ethyl-2-hepten-4-one derived from 5-ethyl-2-hepten-4-ol, 4,6-dimethyl-E-4-octen-3-one derived from 4,6-dimethyl-E-4-octen-3-ol, 4,6,10-trimethyl-E,E-2,4-dodecadien-7-one derived from 4,6,10-trimethyl-E,E-2,4-dodecadien-7-ol, and 7-ethyl-4-pentadecen-6-one derived from 7-ethyl-4-pentadecen-6-ol.

Examples of the cyclic saturated ketones include cyclopentanone derived from cyclopentanol, 2-methylcyclopentanone derived from 2-methylcyclopentanol, cyclohexanone derived from cyclohexanol, 4-tert-butylcyclohexanone derived from 4-tert-butylcyclohexanol, and menthone derived from L-menthol.

Examples of the cyclic unsaturated ketones include 2-cyclohexenone derived from 2-cyclohexenol, 3-cyclohexenone derived from 3-cyclohexenol, 3-methyl-2-cyclohexen-1-one derived from 3-methyl-2-cyclohexen-1-ol, 3,3,5-trimethylcyclohexen-2-one derived from 3,3,5-trimethylcyclohexen-2-ol, and 6-isopropyl-3-methylcyclohexen-2-one derived from 6-isopropyl-3-methylcyclohexen-2-ol.

The polymeric carbodiimide that is used in the method for producing an aldehyde or a ketone, is a compound represented by formula (1):

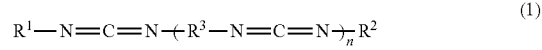

(1)

wherein $R^1$ and $R^2$, which may be identical with or different from each other, each represents a substituted or unsubstituted, linear or branched alkyl group having 1 to 12 carbon atoms, a substituted or unsubstituted cycloalkyl group having 3 to 12 carbon atoms, or a substituted or unsubstituted aryl group having 6 to 12 carbon atoms; R3 represents a substituted or unsubstituted, linear or branched alkylene group having 1 to 12 carbon atoms, a substituted or unsubstituted cycloalkylene group having 3 to 12 carbon atoms, a substituted or unsubstituted arylene group having 6 to 12 carbon atoms, a substituted or unsubstituted alkylenecycloalkylene group having 4 to 18 carbon atoms, or a substituted or unsubstituted alkylenearylene group having 7 to 18 carbon atoms; and n represents a number that satisfies the molecular weight described above.

Examples of the substituents $R^1$ and $R^2$ include an alkyl group such as a methyl group, an ethyl group, an n-propyl group, an isopropyl group, an n-butyl group, a t-butyl group or an isobutyl group; a cycloalkyl group such as a cyclopentyl group or a cyclohexyl group; and an aryl group such as a phenyl group, a biphenyl group or a naphthyl group, and particularly, a cyclohexyl group is preferred.

Examples of the substituent $R^3$ include an alkylene group, a cycloalkylene group, an alkylenecycloalkylene group, an arylene group, and an alkylenearylene group.

Examples of the alkylene group for $R^3$ include a methylene group, an ethylene group, a propylene group, a butylene group, a pentylene group and a hexylene group.

Examples of the cycloalkylene group for $R^3$ include a cyclopentylene group and a cyclohexylene group.

Examples of the alkylenecycloalkylene group for $R^3$ include a cyclohexylenemethylene group such as a 1,3-cyclohexylenemethylene group or a 1,4-cyclohexylenemethylene group; a cyclohexyleneethylene group; a dicyclohexylenemethylene group such as a 4,4'-dicyclohexylenemethylene group; a dicyclohexyleneethylene group; a cyclohexylenedimethylene group; and a cyclohexylenediethylene group.

Examples of the arylene group for $R^3$ include a phenylene group, and a biphenylene group.

Examples of the alkylenearylene group for $R^3$ include a phenylenemethylene group, a phenyleneethylene group, a diphenylenemethylene group, a diphenyleneethylene group, and a phenylenedimethylene group.

The unsubstituted $R^3$ is particularly preferably a dicyclohexylenemethylene group, a cyclohexylenemethylene group, or a phenylenedimethylene group.

Preferred examples of the substituent that may be carried by $R^1$, $R^2$ and $R^3$ include an alkyl group having 1 to 4 carbon atoms, such as a methyl group, an ethyl group, a propyl group, an isopropyl group or an isobutyl group (provided that the cases in which $R^1$, $R^2$ and $R^3$ themselves are alkyl groups are excluded); an alkoxy group having 1 to 4 carbon atoms, such as a methoxy group, an ethoxy group or a propoxy group; a halogen group such as chlorine or bromine; and an acetoxy group.

Examples of the substituted R3 include a 3,5,5-trimethyl-1,3-cyclohexylenemethylene group, an α,α,α',α'-meta-tetramethylxylylene group, and an α,α,α',α'-para-tetramethylxylylene group.

Preferred specific examples of the polymeric carbodiimide represented by the formula (1) will be described below.

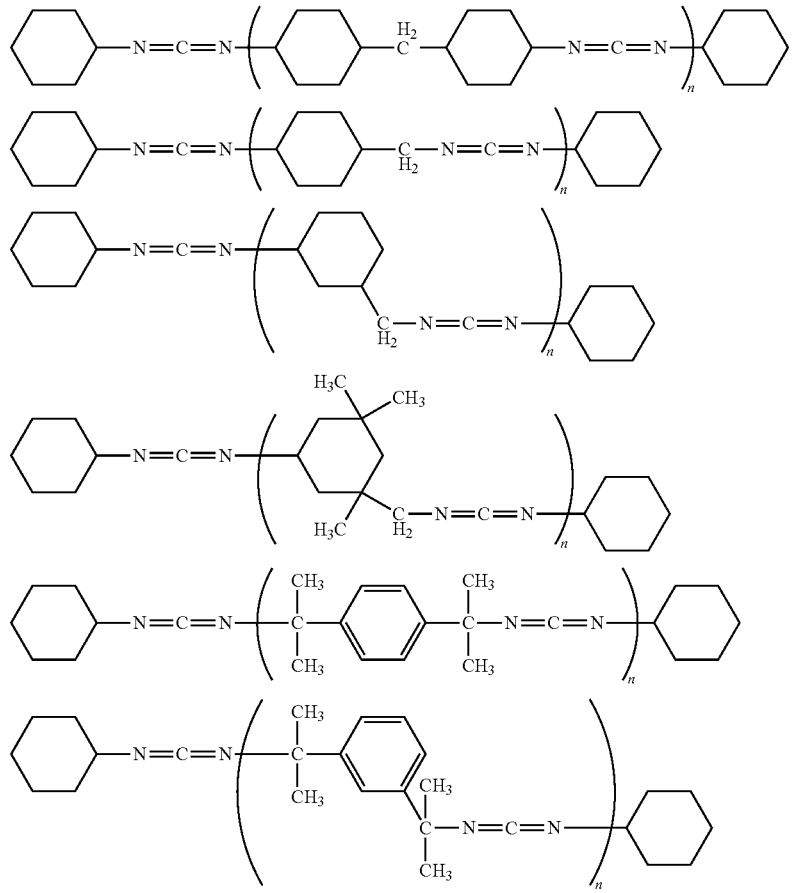

An example of commercially available products of the polymeric carbodiimide may be Carbodilite (registered trademark) V-03 (50% by weight polymeric carbodiimide/toluene solution: a product of Nisshinbo Chemical Inc.), in which $R^1$ and $R^2$ are cyclohexyl groups, and $R^3$ is a 4,4'-dicyclohexylene-methylene group.

The weight-average molecular weight of the polymeric carbodiimide is 300 to 5000, preferably 2000 to 3000, from the viewpoint of the dissolubility of the carbodiimide in solvents. The weight-average molecular weight of the polymeric carbodiimide can be obtained by using gel permeation chromatography (GPC) based on polystyrene standards.

As a byproduct of the oxidation reaction of an alcohol, a urea compound is produced from the carbodiimide compound. When a polymeric carbodiimide is used, this urea compound is thought to be a compound represented by the following formula (5), in which the carbodiimide bond in the polymeric carbodiimide has been converted to a urea bond.

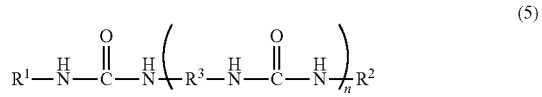

(5)

wherein $R^1$, $R^2$, $R^3$ and n have the same definitions as defined above.

There is no particular limitation on the amount of the polymeric carbodiimide. From the viewpoint of reactivity or productivity, the amount is preferably 1.2 to 5.0 moles, particularly preferably 1.5 to 2.0 moles, relative to 1 mole of the raw material alcohol, in terms of the carbodiimide equivalent in the polymeric carbodiimide.

The polymeric carbodiimide is preferably used after being dissolved in an organic solvent.

The organic solvent that is used to dissolve the polymeric carbodiimide is not particularly limited as long as it does not have any adverse effect on the reaction by dissolving the polymeric carbodiimide. The organic solvent is preferably an organic solvent in which the urea compound generated from the carbodiimide as a byproduct of the oxidation reaction of an alcohol is insoluble. It is because the urea compound can be easily removed by filtration or the like. Examples of the organic solvent include aromatic solvents such as toluene, xylene and benzene; halogen-based solvents such as chloroform, methylene chloride and trichloroethylene; acetone, methyl ethyl ketone, tetrahydrofuran, N,N-dimethylformamide, N,N-dimethylacetamide and dimethyl sulfoxide, and among them, toluene is particularly preferred. These solvents may be used singly, or may be used as solvent mixtures of two or more kinds.

It is preferable that an organic solvent can dissolve not only the polymeric carbodiimides, but also primary or secondary alcohols, sulfoxides, acids and bases. When a primary alcohol or a secondary alcohol is oxidized in the presence of an organic solvent solution of the polymeric carbodiimide, a sulfoxide compound, an acid and a base, a uniform phase is formed during the reaction and the reactivity is enhanced as compared with the conventionally known water-soluble carbodiimides or N-alkylcarbodiimide polystyrene resins.

Dimethyl sulfoxide, which is included by the examples of the sulfoxide compound that will be described below, can also be used as a solvent for dissolving the polymeric carbodiimide.

There is no particular limitation on the amount of the organic solvent. The amount is preferably 50 to 500 ml, more preferably 100 to 300 ml, relative to 1 mole of the raw material alcohol. Furthermore, in the case where the organic solvent also serves as a sulfoxide compound, the amount is preferably 100 to 3000 ml, more preferably 500 to 1000 ml, relative to 1 mole of the raw material alcohol.

The oxidation reaction is carried out in the presence of a polymeric carbodiimide, a sulfoxide compound, an acid and a base, or a salt of the acid and the base.

The sulfoxide compound is a compound represented by the following formula (4):

$$CH_3(R^7)S=O \qquad (4)$$

wherein $R^7$ represents a linear, branched or cyclic hydrocarbon group having 1 to 12 carbon atoms.

The sulfoxide compound is preferably, but not limited to, dimethyl sulfoxide that is generally used in Pfitzner-Moffatt oxidation. When the foul odor of dimethyl sulfide as a byproduct causes a problem after the reaction, a sulfoxide compound having a larger molecular weight and causing less effect of foul odor can be used.

Specific examples of the sulfoxide compound include dimethyl sulfoxide, ethyl methyl sulfoxide, propyl methyl sulfoxide, butyl methyl sulfoxide, pentyl methyl sulfoxide, and dodecyl methyl sulfoxide. These may be used singly, or two or more kinds may be used in combination.

There is no particular limitation on the amount of the sulfoxide compound. From the viewpoints of reactivity and productivity, the amount is preferably 0.5 to 50.0 moles, more preferably 10.0 to 20.0 moles, relative to 1 mole of the raw material alcohol.

With regard to the acid, preferred examples include trifluoroacetic acid, difluoroacetic acid, trichloroacetic acid, dichloroacetic acid, monochloroacetic acid, cyanoacetic acid, anhydrous orthophosphoric acid, and phosphorous acid. Among them, trifluoroacetic acid, dichloroacetic acid, and anhydrous orthophosphoric acid are particularly preferred. These may be used singly, or two or more kinds may be used in combination.

There is no particular limitation on the amount of the acid. From the viewpoints of reactivity and the amount of impurity as a byproduct, the amount is preferably 0.3 to 2.0 moles, more preferably 0.3 to 0.5 moles, relative to 1 mole of the raw material alcohol.

With regard to the base, examples include pyridine, quinoline, triethylamine, aniline, morpholine and piperidine, and pyridine is particularly preferred. From the viewpoints of reactivity and the amount of impurity as a byproduct, the amount of the base is preferably 0.5 to 3.0 moles, more preferably 0.8 to 1.0 moles, relative to 1 mole of the raw material alcohol.

When a primary or secondary alcohol is oxidized in the presence of a polymeric carbodiimide, a sulfoxide, an acid and a base, and an optional organic solvent, it is preferable, from the viewpoint of reactivity, to add an organic solvent solution of the polymeric carbodiimide to a mixture of the primary or secondary alcohol, the sulfoxide, the acid, the base and the optional organic solvent.

Since an acid and a base are used together, a salt formed from the acid and the base may be present in the system. Furthermore, it is also possible to use a salt formed from the acid and the base, in place of the acid and the base. For example, a pyridinium salt of trifluoroacetic acid can be used in place of pyridine and trifluoroacetic acid. In general, it is preferable to use an acid and a base.

In regard to the reaction mechanism, it is speculated that when H+ originating from the acid initially activates the polymeric carbodiimide, the activated carbodiimide reacts with, for example, dimethyl sulfoxide to produce an active species. This active species reacts with the alcohol to produce urea as a byproduct, and finally, an aldehyde is released to produce dimethyl sulfide. The base is believed to have a role of extracting H+ in the final stage of aldehyde production.

The reaction temperature of the oxidation reaction is not particularly limited. From the viewpoints of the effectiveness of the reaction that is carried out under mild conditions at near room temperature, and the controllability of impurity as a byproduct, the reaction temperature is preferably 10 to 30° C., more preferably 20 to 25° C.

The reaction time of the oxidation is not particularly limited. It is preferably 3 to 10 hours, more preferably 5 to 6 hours, from the viewpoint of productivity.

EXAMPLES

Hereinafter, the present invention will be described more specifically by way of Examples. It should not be construed that the present invention is limited to the Examples.

Example 1

In a reactor equipped with a stirrer, a cooling condenser, a dropping funnel and a thermometer, E,Z-4,6-hexadecadienyl alcohol (119.2 g, 0.50 mol), dimethyl sulfoxide (586 g, 7.50 mol) and toluene (200 g) were placed, and the resulting reaction solution was stirred at a temperature of 20 to 23° C. To this reaction solution, pyridine (39.6 g, 0.50 mol) was added dropwise, followed by trifluoroacetic acid (28.5 g, 0.25 mol). The resulting mixture was maintained at a temperature of 25° C. or lower and was stirred for 10 minutes. After stirring, Carbodilite V-03 (manufactured by Nisshinbo Chemical Inc., 431.1 g/mol) (431.1 g; 1.0 mol) was added dropwise to the reaction liquid, while the reaction liquid was maintained at 25° C. or below. After the dropwise addition, the reaction liquid was stirred for 5 hours at 23 to 25° C., and the reaction was terminated with a 1.0% aqueous solution of acetic acid (80 g). After the reaction was terminated, a urea compound precipitated from the reaction liquid was separated by filtration. The filtrate was partitioned to remove the aqueous phase, and then the organic phase was washed with an aqueous sodium chloride solution.

The resulting organic phase was treated such that the solvent was removed under reduced pressure, and the residue was distilled under reduced pressure. Thus, E,Z-4,6-hexadecadienyl aldehyde (bp: 123 to 128° C./0.27 kPa, 98.0 g, 0.41 mol) was obtained (yield 82.9%). The aldehyde compound thus obtained was confirmed by using NMR, mass spectrometry and IR spectroscopy.

Example 2

In a reactor equipped with a stirrer, a cooling condenser, a dropping funnel and a thermometer, Z,Z-7,11-hexadecadienyl alcohol (71.5 g, 0.30 mol), dimethyl sulfoxide (352 g, 4.50 mol) and toluene (120 g) were placed, and the resulting reaction solution was stirred at a temperature of 20 to 23° C. To this reaction solution, pyridine (23.7 g, 0.30 mol) was added dropwise, followed by trifluoroacetic acid (17.1 g, 0.15 mol). The resulting mixture was maintained at a temperature of 25° C. or lower and was stirred for 10 minutes. After stirring, Carbodilite V-03 (manufactured by Nisshinbo Chemical Inc., 431.1 g/mol) (258.7 g, 0.60 mol) was added dropwise to the reaction liquid, while the reaction liquid was maintained at 25° C. or below. After the dropwise addition, the reaction liquid was stirred for 5 hours at 23 to 25° C., and the reaction was terminated with a 1.0% aqueous solution of acetic acid (48 g). After the reaction was terminated, a urea compound precipitated from the reaction liquid was separated by filtration. The filtrate was partitioned to remove the aqueous phase, and then the organic phase was washed with an aqueous sodium chloride solution.

The resulting organic phase was treated such that the solvent was removed under reduced pressure, and the residue was distilled under reduced pressure. Thus, Z,Z-7,11-hexadecadienyl aldehyde (bp: 112 to 117° C./0.27 kPa, 65.3 g, 0.28 mol) was obtained (yield 99.0%). The aldehyde compound thus obtained was confirmed by using NMR, mass spectrometry and IR spectroscopy.

Example 3

In a reactor equipped with a stirrer, a cooling condenser, a dropping funnel and a thermometer, Z-11-hexadecenyl alcohol (72.1 g, 0.30 mol), dimethyl sulfoxide (352 g, 4.50 mol) and toluene (120 g) were added, and the resulting reaction solution was stirred at a temperature of 20 to 23° C. To this reaction solution, pyridine (23.7 g, 0.30 mol) was added dropwise, followed by trifluoroacetic acid (17.1 g, 0.15 mol). The resulting mixture was maintained at a temperature of 25° C. or lower and was stirred for 10 minutes. After stirring, Carbodilite V-03 (manufactured by Nisshinbo Chemical Inc., 431.1 g/mol) (258.7 g, 0.60 mol) was added dropwise to the reaction liquid, while the reaction liquid was maintained at 25° C. or below. After the dropwise addition, the reaction liquid was stirred for 5 hours at 23 to 25° C., and the reaction was terminated with a 1.0% aqueous solution of acetic acid (48 g). After the reaction was terminated, a urea compound precipitated from the reaction liquid was separated by filtration. The filtrate was partitioned to remove the aqueous phase, and then the organic phase was washed with an aqueous sodium chloride solution.

The resulting organic phase was treated such that the solvent was removed under reduced pressure, and the residue was distilled under reduced pressure. Thus, Z-11-hexadecenyl aldehyde (bp: 114 to 120° C./0.27 kPa, 59.6 g, 0.25 mol) was obtained (yield 83.4%). The aldehyde compound thus obtained was confirmed by using NMR, mass spectrometry and IR spectroscopy.

Example 4

In a reactor equipped with a stirrer, a cooling condenser, a dropping funnel and a thermometer, citronellol (46.9 g, 0.30 mol), dimethyl sulfoxide (352 g, 4.50 mol) and toluene (120 g) were added, and the resulting reaction solution was stirred at a temperature of 20 to 23° C. To this reaction solution, pyridine (23.7 g, 0.30 mol) was added dropwise, followed by trifluoroacetic acid (17.1 g, 0.15 mol). The resulting mixture was maintained at a temperature of 25° C. or lower and was stirred for 10 minutes. After stirring, Carbodilite V-03 (manufactured by Nisshinbo Chemical Inc., 431.1 g/mol) (258.7 g, 0.60 mol) was added dropwise to the reaction liquid, while the reaction liquid was maintained at 25° C. or below. After the dropwise addition, the reaction liquid was stirred for 5 hours at 23 to 25° C., and the reaction was terminated with a 1.0% aqueous solution of acetic acid (48 g). After the reaction was terminated, a urea compound precipitated from the reaction liquid was separated by filtration. The filtrate was partitioned to remove the aqueous phase, and then the organic phase was washed with an aqueous sodium chloride solution.

The resulting organic phase was treated such that the solvent was removed under reduced pressure, and the residue was distilled under reduced pressure. Thus, citronellal (bp: 76 to 78° C./0.27 kPa, 34.6 g, 0.22 mol) was obtained (yield 74.7%). The aldehyde compound thus obtained was confirmed by using NMR, mass spectrometry and IR spectroscopy.

Example 5

In a reactor equipped with a stirrer, a cooling condenser, a dropping funnel and a thermometer, 1-dodecyl alcohol (55.9 g, 0.30 mol), dimethyl sulfoxide (352 g, 4.50 mol) and toluene (120 g) were added, and the resulting reaction solution was stirred at a temperature of 20 to 23° C. To this reaction solution, pyridine (23.7 g, 0.30 mol) was added dropwise, followed by trifluoroacetic acid (17.1 g, 0.15 mol). The resulting mixture was maintained at a temperature of 25° C. or lower and was stirred for 10 minutes. After stirring, Carbodilite V-03 (manufactured by Nisshinbo Chemical Inc., 431.1 g/mol) (258.7 g, 0.60 mol) was added dropwise to the reaction liquid, while the reaction liquid was maintained at 25° C. or below. After the dropwise addition, the reaction liquid was stirred for 5 hours at 23 to 25° C., and the reaction was terminated with a 1.0% aqueous solution of acetic acid (48 g). After the reaction was terminated, a urea compound precipitated from the reaction liquid was separated by filtration. The filtrate was partitioned to remove the aqueous phase, and then the organic phase was washed with brine.

The resulting organic layer was treated such that the solvent was removed under reduced pressure, and the residue was distilled under reduced pressure. Thus, 1-dodecyl aldehyde (bp: 75 to 78° C./0.27 kPa, 39.4 g, 0.21 mol) was obtained (yield 71.3%). The aldehyde compound thus obtained was confirmed by using NMR, mass spectrometry and IR spectroscopy.

Example 6

In a reactor equipped with a stirrer, a cooling condenser, a dropping funnel and a thermometer, 4-tert-butylcyclohexanol (15.6 g, 0.10 mol), dimethyl sulfoxide (117.2 g, 1.50 mol) and toluene (40 g) were added, and the resulting reaction solution was stirred at a temperature of 20 to 23° C. To this reaction solution, pyridine (7.9 g, 0.10 mol) was added dropwise, followed by dichloroacetic acid (6.4 g, 0.05 mol). The resulting mixture was maintained at a temperature of 25° C. or lower and was stirred for 10 minutes. After stirring, Carbodilite V-03 (manufactured by Nisshinbo Chemical Inc., 431.1 g/mol) (86.2 g, 0.20 mol) was added dropwise to the reaction liquid, while the reaction liquid was maintained at 25° C. or below. After the dropwise addition, the reaction liquid was stirred for 5 hours at 23 to 25° C., and the reaction was terminated with a 1.0% aqueous solution of acetic acid (16 g). After the reaction was terminated, a urea compound precipitated from the reaction liquid was separated by filtration. The filtrate was partitioned to remove the aqueous phase, and then the organic phase was washed with an aqueous sodium chloride solution.

The resulting organic layer was treated such that the solvent was removed under reduced pressure, and the residue was distilled under reduced pressure. Thus, 4-tert-butylcyclohexanone (bp: 88 to 90° C./1.06 kPa, 14.1 g, 0.09 mol) was obtained (yield 91.3%). The ketone compound thus obtained was confirmed by using NMR, mass spectrometry and IR spectroscopy.

Example 7

In a reactor equipped with a stirrer, a cooling condenser, a dropping funnel and a thermometer, L-menthol (15.6 g, 0.10 mol), dimethyl sulfoxide (117.2 g, 1.50 mol) and toluene (40 g) were added, and the resulting reaction solution was stirred at a temperature of 20 to 23° C. To this reaction solution, pyridine (7.9 g, 0.10 mol) was added dropwise, followed by dichloroacetic acid (6.4 g, 0.05 mol). The resulting mixture was maintained at a temperature of 25° C. or lower and was stirred for 10 minutes. After stirring, Carbodilite V-03 (manufactured by Nisshinbo Chemical Inc., 431.1 g/mol) (86.2 g, 0.20 mol) was added dropwise to the reaction liquid, while the reaction liquid was maintained at 25° C. or below. After the dropwise addition, the reaction liquid was stirred for 5 hours at 23 to 25° C., and the reaction was terminated with a 1.0% aqueous solution of acetic acid (16 g). After the reaction was terminated, a urea compound precipitated from the reaction liquid was separated by filtration. The filtrate was partitioned to remove the aqueous phase, and then the organic phase was washed with an aqueous sodium chloride solution.

The resulting organic layer was treated such that the solvent was removed under reduced pressure, and the residue was distilled under reduced pressure. Thus, menthone (bp: 82 to 85° C./1.33 kPa, 12.3 g, 0.08 mol) was obtained (yield 79.7%). The ketone compound thus obtained was confirmed by using NMR, mass spectrometry and IR spectroscopy.

Comparative Example 1

In a reactor equipped with a stirrer, a cooling condenser, a dropping funnel and a thermometer, E,Z-4,6-hexadecadienyl alcohol (23.8 g, 0.10 mol), dimethyl sulfoxide (117 g, 1.50 mol) and toluene (20 g) were added, and the resulting reaction solution was stirred at a temperature of 20 to 23° C. To this reaction solution, pyridine (7.9 g, 0.10 mol) was added dropwise, followed by trifluoroacetic acid (6.4 g, 0.05 mol). The resulting mixture was maintained at a temperature of 25° C. or lower and was stirred for 10 minutes. After stirring, a suspension of 1-ethyl-3-(3-N,N-dimethylaminopropyl)-carbodiimide (EPCI, 38.2 g, 0.20 mol) in toluene (50 g) was added dropwise to the reaction liquid, while the reaction liquid was maintained at 25° C. or below. After the dropwise addition, the reaction liquid was stirred for 28 hours at 23 to 25° C., and the reaction was terminated with a 1.0% aqueous solution of acetic acid (16 g). After the reaction was terminated, the reaction liquid was partitioned to remove the aqueous phase, and then the organic phaser was repeatedly washed with an aqueous sodium chloride solution.

The resulting organic phase was treated such that the solvent was removed under reduced pressure, and the residue was distilled under reduced pressure. Thus, E,Z-4,6-hexadecadienyl aldehyde (bp: 125 to 132° C./0.27 kPa, 14.7 g, 0.06 mol) was obtained (yield 62.3%). The aldehyde compound thus obtained was confirmed by using NMR, mass spectrometry and IR spectroscopy.

Comparative Example 2

In a reactor equipped with a stirrer, a cooling condenser, a dropping funnel and a thermometer, E,Z-4,6-hexadecadienyl alcohol (0.72 g, 3.0 mmol), dimethyl sulfoxide (3.52 g, 45 mmol) and toluene (4.00 g) were added, and the resulting reaction solution was stirred at a temperature of 20 to 23° C. To this reaction solution, pyridine (0.24 g, 3.0 mmol) was added dropwise at 25° C. or below, followed by trifluoroacetic acid (0.17 g, 1.5 mmol). The resulting mixture was stirred for 10 minutes. After stirring, an N-cyclohexylcarbodiimide polystyrene resin (manufactured by Tokyo Chemical Industry Co., Ltd., 666.7 g/mol) (4.0 g, 6.0 mmol) was added, while the reaction liquid was maintained at 25° C. or below. After the dropwise addition, the reaction liquid was stirred for 8 hours at 23 to 25° C., and the reaction was terminated with a 1.0% aqueous solution of acetic acid (3 g). After the reaction was terminated, the reaction liquid was filtered, the filtrate was partitioned to remove the aqueous phase, and then the organic phase was washed with an aqueous sodium chloride solution.

The resulting organic phase was treated such that the solvent was removed under reduced pressure, and the residue was purified by silica gel column chromatography (eluent n-hexane:ethyl acetate=20:1). Thus, E,Z-4,6-hexadecadienyl aldehyde (0.34 g, 1.45 mmol) was obtained (yield 48.2%). The aldehyde compound thus obtained was confirmed by using NMR, mass spectrometry and IR spectroscopy.

The invention claimed is:

1. A method for producing an aldehyde or a ketone, the method comprising at least an oxidation step of oxidizing a primary alcohol or a secondary alcohol in the presence of a polymeric carbodiimide having a weight-average molecular weight of 300 to 5000, being soluble in an organic solvent and being represented by the following formula (1):

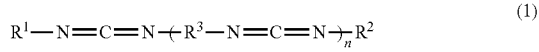
(1)

wherein R1 and R2, which may be identical with or different from each other, each represents a substituted or unsubstituted, linear or branched alkyl group having 1 to 12 carbon atoms, a substituted or unsubstituted cycloalkyl group having 3 to 12 carbon atoms, or a substituted or unsubstituted aryl group having 6 to 12 carbon atoms; R3 represents a substituted or unsubstituted, linear or branched alkylene group having 1 to 12 carbon atoms, a substituted or unsubstituted cycloalkylene group having 3 to 12 carbon atoms, a substituted or unsubstituted arylene group having 6 to 12 carbon atoms, a substituted or unsubstituted alkylenecycloalkylene group having 4 to 18 carbon atoms, or a substituted or unsubstituted alkylenearylene group having 7 to 18 carbon atoms; and n represents a number that satisfies the molecular weight described above,
and a sulfoxide compound, together with an acid and a base or together with a salt of the acid and the base.

2. The method for producing an aldehyde or a ketone according to claim 1, wherein said oxidation step is carried out in the presence of an organic solvent in which an urea compound produced during the oxidation as a byproduct is insoluble.

3. The method for producing an aldehyde or a ketone according to claim 1, wherein said primary alcohol and said secondary alcohol are compounds represented by the following formula (2) and formula (3), respectively:

wherein R4 represents a linear, branched or cyclic hydrocarbon group having 1 to 20 carbon atoms; and R5 and R6, which may be identical with or different from each other, each independently represents a linear, branched or cyclic hydrocarbon group having 1 to 20 carbon atoms, or may be joined together to form a ring.

4. The method for producing an aldehyde or a ketone according to claim 2, wherein said primary alcohol and said secondary alcohol are compounds represented by the following formula (2) and formula (3), respectively:

wherein R4 represents a linear, branched or cyclic hydrocarbon group having 1 to 20 carbon atoms; and R5 and R6, which may be identical with or different from each other, each independently represents a linear, branched or cyclic hydrocarbon group having 1 to 20 carbon atoms, or may be joined together to form a ring.

5. The method for producing an aldehyde or a ketone according to claim 1, wherein said sulfoxide compound is represented by the following formula (4):

wherein R7 represents a linear, branched or cyclic hydrocarbon group having 1 to 12 carbon atoms.

6. The method for producing an aldehyde or a ketone according to claim 2, wherein said sulfoxide compound is represented by the following formula (4):

CH3(R7)S═O (4)

wherein R7 represents a linear, branched or cyclic hydrocarbon group having 1 to 12 carbon atoms.

7. The method for producing an aldehyde or a ketone according to claim 3, wherein said sulfoxide compound is represented by the following formula (4):

wherein R7 represents a linear, branched or cyclic hydrocarbon group having 1 to 12 carbon atoms.

8. The method for producing an aldehyde or a ketone according to claim 4, wherein said sulfoxide compound is represented by the following formula (4):

wherein R7 represents a linear, branched or cyclic hydrocarbon group having 1 to 12 carbon atoms.

9. The method for producing an aldehyde or a ketone according to claim 1, wherein said acid is selected from the group consisting of trifluoroacetic acid, difluoroacetic acid, trichloroacetic acid, dichloroacetic acid, monochloroacetic acid, cyanoacetic acid, anhydrous orthophosphoric acid, and phosphorous acid.

10. The method for producing an aldehyde or a ketone according to claim 2, wherein said acid is selected from the group consisting of trifluoroacetic acid, difluoroacetic acid, trichloroacetic acid, dichloroacetic acid, monochloroacetic acid, cyanoacetic acid, anhydrous orthophosphoric acid, and phosphorous acid.

11. The method for producing an aldehyde or a ketone according to claim 4, wherein said acid is selected from the group consisting of trifluoroacetic acid, difluoroacetic acid, trichloroacetic acid, dichloroacetic acid, monochloroacetic acid, cyanoacetic acid, anhydrous orthophosphoric acid, and phosphorous acid.

12. The method for producing an aldehyde or a ketone according to claim 5, wherein said acid is selected from the group consisting of trifluoroacetic acid, difluoroacetic acid, trichloroacetic acid, dichloroacetic acid, monochloroacetic acid, cyanoacetic acid, anhydrous orthophosphoric acid, and phosphorous acid.

13. The method for producing an aldehyde or a ketone according to claim 1, wherein said base is selected from the group consisting of pyridine, quinoline, triethylamine, aniline, morpholine and piperidine.

14. The method for producing an aldehyde or a ketone according to claim 2, wherein said base is selected from the group consisting of pyridine, quinoline, triethylamine, aniline, morpholine and piperidine.

15. The method for producing an aldehyde or a ketone according to claim 3, wherein said base is selected from the group consisting of pyridine, quinoline, triethylamine, aniline, morpholine and piperidine.

16. The method for producing an aldehyde or a ketone according to claim 7, wherein said base is selected from the group consisting of pyridine, quinoline, triethylamine, aniline, morpholine and piperidine.

17. The method for producing an aldehyde or a ketone according to claim 13, wherein said base is selected from the group consisting of pyridine, quinoline, triethylamine, aniline, morpholine and piperidine.

* * * * *